United States Patent
Suh et al.

(10) Patent No.: US 7,081,485 B2
(45) Date of Patent: Jul. 25, 2006

(54) NON-VOLATILE DENTAL COMPOSITIONS CONTAINING MULTIFUNCTIONAL ACRYLATE COMPOUNDS AND LACKING AN OXYGEN-INHIBITED LAYER

(75) Inventors: Byoung I Suh, Oak Brook, IL (US); Li Feng, Naperville, IL (US)

(73) Assignee: Bisco, Inc., Schaumburg, IL (US)

( * ) Notice: Subject to any disclaimer, the term of this patent is extended or adjusted under 35 U.S.C. 154(b) by 241 days.

(21) Appl. No.: 10/224,795

(22) Filed: Aug. 21, 2002

(65) Prior Publication Data

US 2004/0039078 A1    Feb. 26, 2004

(51) Int. Cl.
*A61K 6/083* (2006.01)
*C08F 2/46* (2006.01)

(52) U.S. Cl. .................. 522/28; 522/186; 523/115; 523/116; 523/118; 524/492

(58) Field of Classification Search .............. 522/28, 522/186; 523/115, 116, 118; 524/492
See application file for complete search history.

(56) References Cited

U.S. PATENT DOCUMENTS

| | | | | |
|---|---|---|---|---|
| 4,199,421 A | * | 4/1980 | Kamada et al. | 522/168 |
| 4,454,258 A | * | 6/1984 | Kawahara et al. | 523/116 |
| 6,057,383 A | * | 5/2000 | Volkel et al. | 523/116 |
| 6,197,844 B1 | * | 3/2001 | Hamrock et al. | 522/167 |
| 6,326,417 B1 | * | 12/2001 | Jia | 523/116 |
| 2002/0121631 A1 | * | 9/2002 | Rahman et al. | |
| 2003/0060534 A1 | | 3/2003 | Fukushima et al. | 523/115 |
| 2003/0207960 A1 | * | 11/2003 | Jia | |

FOREIGN PATENT DOCUMENTS

| | | |
|---|---|---|
| EP | 0 173 567 A | 3/1986 |
| EP | 0 980 682 A1 | 2/2000 |
| JP | 362129211 A * | 6/1987 |
| JP | WO 02/05752 A1 | 1/2002 |

OTHER PUBLICATIONS

Yuji Nishiwaki et al.; "Cross-Sectional Study of Health Effects of Methyl Methacrulate Monomer among Dental Laboratory Technicians;" *J. Occup. Health*, 43: 375-378; 2001.
U.S. Environmental Protection Agency (7407); "Pollution Prevention and Toxics;" Nov. 1994.
Sadoh DR, et al.; "Generalised neuropathy following exposure to methyl methacrylate monomer;" *British Dental Journal*, 186 (8): 380-381; 1999.
Trademark Electronic Search System record for EXTORAL; Serial No. 73/747,832; registered Sep. 19, 1989.

* cited by examiner

*Primary Examiner*—Tae H. Yoon
(74) *Attorney, Agent, or Firm*—Homer W. Faucett, III; Richard A. Schnurr; Ice Miller LLP

(57) ABSTRACT

Dental composite formulations containing an initiator and a multiacrylate compound are disclosed. The formulations lack methyl methacrylate, a volatile, irritating, and potentially hazardous material commonly found in dental formulations. The multiacrylate compound has at least three acrylate functionalities per molecule. The formulations cure to form a surface lacking an oxygen inhibition layer. The formulations can be used as dental sealants, dental coatings, and in fingernail/toenail repair applications.

22 Claims, No Drawings

NON-VOLATILE DENTAL COMPOSITIONS CONTAINING MULTIFUNCTIONAL ACRYLATE COMPOUNDS AND LACKING AN OXYGEN-INHIBITED LAYER

FIELD OF THE INVENTION

The invention relates to dental composite materials, and more specifically, to dental composite materials containing multifunctional acrylate compounds while lacking volatile compounds such as methyl methacrylate.

BACKGROUND OF THE INVENTION

Dental sealants and adhesives are widely used in clinical settings. Desirable properties include safety, efficacy, durability, and favorable cosmetic properties. It is preferred that dental compositions be shelf stable, easy to formulate, and that they do not set so rapidly as to make them difficult to apply to a patient.

Dental compositions frequently contain monomers which are polymerized by the dentist or technician (e.g. by light, self-cure, or dual-cure). However, many dental compositions form a problematic "oxygen inhibited layer" (OIL) or "uncured layer" on their surface. This layer's polymerization is inhibited due to the presence of molecular oxygen radicals in ambient air. As a result, incomplete polymerization occurs. Such layer often render the surface sticky or tacky, making the dental composition more difficult to mold or shape. Such incomplete polymerization also tends to lead to lower hardness of the surface and/or no curing if a thin surface is present.

Extoral is a visible-light cured dental resin formulation sold by AFR Imaging Corp. (Portland, Oreg.). Extoral can be used for surface treatment or as a denture resin. Extoral cures rapidly and produces a glossy, hard surface upon irradiation with normal dental light. Extoral is significant in that it does not have an "oxygen inhibited layer", even when cured with low intensity light. One difficulty with using Extoral is its volatility, leading to a very strong odor. The smell is objectionable to both patients and dentists/technicians, making it difficult to use in a laboratory, and nearly impossible to use in a clinical setting. Another difficulty is the very brittle surface created by Extoral, which may limit its use in certain dental applications such as surfaces subject to compressive forces.

Extoral's odor is suggestive of the presence of methyl methacrylate. Methyl methacrylate is a volatile compound used in several dental products. In addition to its unpleasant smell, exposure to methyl methacrylate has been linked to various health concerns. Numbness, paraesthesia, reduced pulmonary function, and reduced respiratory function have been observed in dental technicians who have been chronically exposed to methyl methacrylate (Sadoh, D. R. et al., *British Dental J.* 186(8): 380–381, 1999; Nishiwaki, Y. et al., *J. Occup. Health* 43: 375–378, 2001). The U.S. Environmental Protection Agency describes methyl methacrylate as an irritant of the nose and throat, and mentions that exposure for short periods of time can cause headache and fatigue (EPA 749-F-95-014 Fact Sheet, November 1994).

It would be of great value to develop a dental composition that does not have an "oxygen inhibited layer" and that does not contain methyl methacrylate or other volatile compounds that are irritating and potentially dangerous to dentists, dental technicians, and their patients.

SUMMARY OF THE INVENTION

An embodiment of the invention is directed towards dental acrylic compositions containing a multiacrylate compound and an initiator. Curing of the compositions results in surfaces lacking an oxygen inhibition layer ("OIL"). The formulations do not contain methyl methacrylate, an irritating and potentially harmful material found in many dental formulations. The multiacrylate compound contains at least three acrylate units per molecule. The formulations can further comprise other acrylate compounds, solvents, fillers, nanofillers, diluents, or other materials useful in dental formulations. The formulations are useful in applications such as dental coatings, dental sealants, and fingernail/toenail repair.

DETAILED DESCRIPTION OF THE INVENTION

An embodiment of the invention is directed towards dental acrylic material compositions that cure to form surfaces that lack an oxygen inhibition layer ("OIL"). The compositions preferably do not contain methyl methacrylate. The compositions preferably cure rapidly to form stable, hard, glossy surfaces.

One embodiment of the invention is a dental composition comprising a multiacrylate compound and an initiator. The multiacrylate compound is a chemical compound comprising at least three acrylate functionalities per molecule. The composition preferably does not contain methyl methacrylate. The composition, upon curing, preferably does not form an oxygen inhibition layer.

Presently preferred initiators are phosphine oxide photoinitiators and camphorquinone. Examples of such initiators include 2,4,6-trimethylbenzoyldiphenylphosphine oxide (TPO), TPO-L, Irgacure 819, Darocure 4265, and camphorquinone. It is expected that other initiators capable of photocleavage with or without the need for amine co-initiators will have utility according to the present invention. The initiator can generally be present at any concentration in the composition. The initiator is preferably present at a concentration that will not noticeably discolor the cured composition. Example concentration ranges of the initiator include about 1 weight percent of the composition or less, at least about 1 weight percent of the composition, at least about 2 weight percent of the composition, at least about 3 weight percent of the composition, at least about 4 weight percent of the composition, at least about 5 weight percent of the composition, at least about 6 weight percent of the composition, or at least about 7 weight percent of the composition up to saturation levels of initiator in the composition. Example concentrations of the initiator include about 3 weight percent of the composition, about 6 weight percent of the composition, and about 7 weight percent of the composition up to saturation levels of initiator in the composition. It is also expected that lower concentrations can be provided in the presence of a volatile dental solvent such as acetone that, upon evaporation, provides the desired higher effective initiator concentration in the composition.

The multiacrylate compound can generally be any multiacrylate compound having at least three acrylate functionalities per molecule in relatively close spatial proximity to one another. Examples of such multiacrylate compounds include a hexafunctional aromatic urethane acrylate oligomer, a caprolactone modified dipentaerythritol hexaacrylate, dipentaerythritol pentaacrylate, di-trimethylolpropane tetraacrylate, trimethylolpropane triacrylate, and ethoxylated trimethylolpropane triacrylate. Other multiacrylate compounds comprising three acrylate functionalities per molecule, compounds comprising four acrylate functionalities per molecule, compounds comprising five acrylate functionalities per molecule, compounds comprising six acrylate functionalities per molecule, compounds comprising seven acrylate functionalities per molecule, compounds comprising eight acrylate functionalities per molecule, compounds comprising nine acrylate functionalities per molecule, and compounds comprising ten acrylate functionalities per molecule in relatively close spatial proximity to one another are also expected to have utility according to the present invention. Larger number of oligo-acrylates or polyacrylates could be added to the compositions.

The multiacrylate compound can generally be present at any concentration of the composition. Example concentration ranges include at least about 20 weight percent of the composition and at least about 30 weight percent of the composition. Specific concentration examples include about 20 weight percent, about 30 weight percent, about 40 weight percent, about 50 weight percent, about 60 weight percent, about 70 weight percent, about 80 weight percent, about 90 weight percent, and about 95 weight percent of the composition.

The compositions can further comprise a co-monomer. The co-monomer preferably polymerizes with the multiacrylate compound. The co-monomer can generally be any type of co-monomer, and preferably is a non-volatile acrylate compound with a surface tension that is similar to or higher than that of the selected multifunctional acrylate compound(s) present in the composition. Presently preferred co-monomers include a monoacrylate compound, diacrylate compound, a triacrylate compound, or a tetraacrylate compound. An example monoacrylate is caprolactone acrylate. Example diacrylate compounds are tripropylene glycol diacrylate, ethoxylated bisphenol A diacrylate, polyethylene glycol diacrylate, epoxy diacrylate, urethane dimethacrylate, and urethane diacrylate. An example triacrylate compound is trimethylolpropane triacrylate. An example tetraacrylate is ditrimethylolpropane tetraacrylate. Ethoxylated forms of such acrylates may be preferred due to their relatively higher surface tension.

The composition can further include a volatile, non-reactive solvent. Examples of such solvents include acetone, ethanol and mixtures of acetone and water, ethanol and water and/or acetone, ethanol and water.

The compositions can further comprise fillers, nanofillers, glass particles, or other dental materials. Examples of such fillers include Ox-50, silane-treated Ox-50, glass ionomer powder IXG 1944 RGW from Ferro, which is also a fluoride release agent.

An additional embodiment of the invention is directed towards methods of using the above-described compositions. A method of sealing a surface can comprise obtaining a surface; applying to the surface a composition comprising a multiacrylate compound and an initiator; and curing the composition to obtain a sealed surface. The sealed surface preferably does not contain an oxygen inhibition layer.

The surface can generally be any surface to be sealed, and is presently preferred to be a dental surface, a tooth, a dental implant, an artificial tooth, a bone, a fingernail, or a toenail. Additionally, the surface may be that of a previously applied dental composition such as a dental composite.

The curing can generally be performed by any means sufficient to rapidly cure the composition to form a non-oxygen inhibited layer (NOIL). The curing step is presently preferred to comprise light curing. The light curing can be performed at low light intensity or at high light intensity. The intensity of light is preferably an intensity suitable for use in a dental laboratory or in a dentist's office. Examples of light intensity ranges include less than about 50 mW/cm$^2$, less than about 100 mW/cm$^2$, about 200 mW/cm$^2$ or less, about 300 mW/cm$^2$ or less, about 400 mW/cm$^2$ or less, about 500 mW/cm$^2$ or less, about 600 mW/cm$^2$ or less, about 800 mW/cm$^2$ or less, and about 2000 mW/cm$^2$ or less, it being understood that higher light intensities can also be employed. Specific examples of light intensities include about 50 mW/cm$^2$, about 100 mW/cm$^2$, about 150 mW/cm$^2$, about 200 mW/cm$^2$, about 250 mW/cm$^2$, about 300 mW/cm$^2$, about 350 mW/cm$^2$, about 400 mW/cm$^2$, about 450 mW/cm$^2$, about 500 mW/cm$^2$, about 600 mW/cm$^2$, about 800 mW/cm$^2$, and about 2000 mW/cm$^2$. Higher light intensities may also be used. For example, Bisco's VIP™ Dental Light Curing system using a blue wavelength light source may be employed by the dentist. Light-curing systems for dental laboratories such as the Jeneric-Pentron Cure-Lite Plus light box system or the Triad light box system from Dentsply, Inc. may also be used for dental appliances. Bisco's NTL™ System utilizing its light source without the nitrogen environment may also be used. The time of light curing can generally be any time. Presently preferred time ranges include about two minutes or less, about one minute or less, less than about 30 seconds, less than about 20 seconds, less than about 15 seconds, less than about 10 seconds, and less than about 5 seconds. Specific examples of light curing times include about one minute, about 30 seconds, about 20 seconds, about 15 seconds, about 10 seconds, about 5 seconds, about 3 seconds, about 2 seconds, and about 1 second. Shorter light cure times are generally preferably to shorten patient time for the procedure and for the convenience of the dental practitioner.

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLES

Example 1

Abbreviations Used in the Examples

The following table lists the chemical compounds and abbreviations used throughout the Examples section.

| Abbreviation/product | Chemical name | Commercial source |
|---|---|---|
| BZ | Benzophenone | Sartomer (Exton, PA) |
| CQ | Camphorquinone | Aldrich Chemical |
| CTXO | 2-Chlorotioxanthen-9-one | Aldrich Chemical |
| EDMAB | Ethyl (4-dimethylamino)benzoate | Esschem Company |
| MEHQ | Methylhydroquinone, a polymerization inhibitor | Aldrich Chemical |
| MMA | Methyl methacrylate | Aldrich Chemical |

-continued

| Abbreviation/product | Chemical name | Commercial source |
|---|---|---|
| OX-50 | Fumed silicon dioxide filler | Degussa |
| TMPTMA | Trimethylopropane trimethacrylate | Esschem Company |
| TPO | Lucirin TPO photoinitiator; 2,4,6-trimethylbenzoyldiphenylphosphine oxide | BASF (Mount Olive, NJ) |
| UDMA | Urethane dimethacrylate | Esschem |
| CD 9052 | Trifunctional acid ester | Sartomer (Exton, PA) |
| CN 120 | Epoxy diacrylate | Sartomer (Exton, PA) |
| CN 383 | Monofunctional acrylated amine coinitiator | Sartomer (Exton, PA) |
| CN 975 | Hexafunctional aromatic urethane acrylate oligomer | Sartomer (Exton, PA) |
| CN 983 | Urethane diacrylate | Sartomer (Exton, PA) |
| Kayarad DPCA20 (DP20) | Caprolactone modified dipentaerythritol hexaacrylate | Sartomer (Exton, PA) |
| Kayarad DPCA60 (DP60) | Caprolactone modified dipentaerythritol hexaacrylate | Sartomer (Exton, PA) |
| SR 259 | Polyethylene glycol (200) diacrylate | Sartomer (Exton, PA) |
| SR 306 | Tripropylene glycol diacrylate | Sartomer (Exton, PA) |
| SR 344 | Polyethylene glycol 400 diacrylate | Sartomer (Exton, PA) |
| SR 349 | Ethoxylated bisphenol A diacrylate | Sartomer (Exton, PA) |
| SR 350 | Trimethylolpropane trimethacrylate | Sartomer (Exton, PA) |
| SR 351 | Trimethylolpropane triacrylate | Sartomer (Exton, PA) |
| SR 355 | Ditrimethylolpropane tetraacrylate | Sartomer (Exton, PA) |
| SR 399 | Dipentaerythritol pentaacrylate | Sartomer (Exton, PA) |
| SR 459 | Caprolactone acrylate | Sartomer (Exton, PA) |
| SR 495 | Caprolactone acrylate | Sartomer (Exton, PA) |
| SR 502 | Ethoxylated trimethylolpropane triacrylate | Sartomer (Exton, PA) |
| SR 610 | Polyethylene glycol (600) diacrylate | Sartomer (Exton, PA) |

Example 2

Analysis of Extoral Composition

While Extoral is a commercial product, its composition and ingredients are not publicly known. The strong objectionable odor suggested that Extoral contains methyl methacrylate. The following analytical experiments were performed in an attempt to determine the chemical composition of Extoral.

Evaporation of the volatile components of Extoral produced a viscous resin. About 40% by weight of the composition evaporated. This was assumed to be primarily methyl methacrylate.

FTIR assays of pre- and post-evaporation Extoral revealed several transitions. A peak at 1620 $cm^{-1}$ grows larger upon evaporation of methyl methacrylate. This peak is present in butyl acrylate, but not in butyl methacrylate. An aliphatic double-bond peak shifts from 1635.0 $cm^{-1}$ to 1633.8 $cm^{-1}$ upon evaporation, indicating a transition from a methacrylate-like character to a more acrylate-like character. The FTIR spectrum of Extoral does not suggest the presence of amines.

UV/Vis spectra comparing Extoral with a TPO standard allowed estimated identification and quantification of TPO in Extoral to be about 4%.

Example 3

Addition of a Hexafunctional Acrylate

Compositions were prepared using CN-975, a hexafunctional aromatic urethane acrylate, MMA, and other compounds. Numbers represent the amount of each compound in the composition by weight percent.

| | Composition | | | |
|---|---|---|---|---|
| Compound | AC-10 | AC-10A | AC-11 | AC-11A |
| CN 975 | 17.2 | 16.7 | 68.7 | 67.0 |
| CN 120Z | 51.5 | 50.3 | | |
| MMA | 29.5 | 28.7 | 29.5 | 28.7 |
| TPO | 1.8 | 4.3 | 1.8 | 4.3 |

Compositions AC-10 and AC-11 had sticky surfaces upon curing at 500 $mW/cm^2$ for 5 seconds. FTIR showed that the surface conversion was 47.3% for AC-10 and 47.5% for AC-11, about 16% lower than for Extoral (63.2%). The higher TPO concentration in AC-10A and AC-11A enhanced the curability. The surface conversion was 65.7% for AC-10A and 58.7% for AC-11A.

The surface of cured AC-11A resembles cured Extoral: non-sticky, slick, hard, and glossy.

Example 4

Preparation of "No Oxygen Inhibited Layer" (NOIL) Compositions

NOIL compositions contain at least two components: a multifunctional acrylate and a photo-initiator (such as phosphine oxide). A diluent (such as ethoxylated di- or tri-acrylate) may also be added to enhance handling of the multiacrylate and/or solubility of the initiator. The compositions can contain additional materials such as solvents, polymerizable co-monomers, inhibitors, surfactants, glass filler, fluorescent or phosphorescent compounds, dyes, colorants, fluoride compounds, and other materials used in the dental and orthodontic fields.

Example 5

Preparation of Unfilled Resin Compositions

A mixture of multifunctional-acrylate, diluents, TPO or other initiator, and optionally MEHQ are blended together. The mixture may be heated at 60° C.–62° C. for four hours with stirring or shaking to afford a clear or hazy solution. The haziness, if any, will fade over a few days.

Example 6

Preparation of Filled Resin Compositions

Unfilled resin and filler such as OX 50 are combined as a slurry. The slurry is ground for 30 minutes. The grinding process often introduces air bubbles into the mixture. The bubbles can be removed by centrifugation at >1000×g for 30 minutes to afford an essentially clear solution.

Example 7

Monomers for Use in "No Oxygen Inhibited Layer" (NOIL) Compositions

Multifunctional acrylates and acrylated diluent co-monomers have been found to be effective ingredients in NOIL compositions. The following table lists exemplary compounds that have been found to be useful.

| Trade name | Chemical description | Characteristics |
|---|---|---|
| Multifunctional Acrylates | | |
| CN 975 | Hexafunctional aromatic urethane acrylate | Fast curing, high hardness |
| Kayarad DPCA20 (DP20) | Acrylate of caprolactone modified dipentaerythritol | Fast curing, lower viscosity |
| Kayarad DPCA60 (DP60) | Acrylate of caprolactone modified dipentaerythritol | Fast curing, flexibility |
| Acrylated Co-Monomers | | |
| SR 344 | Polyethylene glycol 400 diacrylate | Hydrophobicity, hardness |
| SR 349 | Ethoxylated bisphenol A diacrylate esters | Hydrophobicity, hardness |
| SR 610 | Polyethylene glycol (600) diacrylate | Low viscosity, flexibility |
| SR 459 | Caprolactone acrylate | Flexibility, hydrophobicity |
| CN 383 | Monofunctional acrylated amine | Very low viscosity, polymerizing rate promoter |
| CD 9052 | Trifunctional acid ester | Adhesion promoter |

Example 8

Preparation of Volatile MMA Compositions Containing a Tetrafunctional Acrylate (AC-23 and -33)

A composition containing 3 g SR355 (ditrimethylolpropane tetraacrylate), 2 g MMA volatile co-monomer, 0.25 g TPO, and 3.5 mg MEHQ was prepared ("AC-23"). The composition had the characteristic strong odor of a composition containing methyl methacrylate (MMA). The composition was coated on white paper and exposed to VIP light source set at 600 mW/cm$^2$ intensity for an exposure time of 30 seconds. An oxygen inhibition layer was detected by finger touch, which revealed a soft surface even after waiting 10 minutes after exposure to the light source. These results suggest that a tetrafunctional acrylate in the presence of a volatile co-monomer MMA was insufficient to prevent formation of an oxygen inhibition layer.

An additional composition containing 1 g CN975, 4 g SR355 (ditrimethylolpropane tetraacrylate), 0.35 g TPO, and 2.5 mg MEHQ was prepared ("AC-33"). The composition had the characteristic strong odor of a composition containing methyl methacrylate (MMA). This composition could not be cured tack-free in less than 60 seconds exposure to the VIP light gun set at 600 mW/cm$^2$, and was easily scratchable even after exposure to that intensity light for 60 seconds.

Example 9

Preparation of a Volatile MMA Composition Containing a Pentafunctional Acrylate (AC-24)

A composition containing 3 g SR399 (dipentaerythritol pentaacrylate esters), 2 g MMA volatile co-monomer, 0.25 g TPO, and 3.5 mg MEHQ was prepared. The composition had the characteristic strong odor of a composition containing methyl methacrylate (MMA). The composition was coated on Pyramid composite, shade 3.5 (Bisco, Inc.) and cured by exposure to the VIP light gun output for 10 seconds at 300 mW/cm$^2$. No oxygen inhibition layer was detected by finger touch, suggesting that a pentafunctional acrylate in the presence of a volatile co-monomer MMA is sufficient to prevent formation of an oxygen inhibition layer.

Example 10

Preparation of Non-volatile NOIL Compositions AC-15C and Filled and Colored AC-15C A composition containing 2.7 g CN975, 3.3 g SR344, 0.333 g TPO, and 3 mg MEHQ was prepared ("AC-15C"). A filled mixture of 75% AC-15C and 25% OX50 filler by weight was also prepared. The AC-15C compositions contain a hexafunctional diacrylate (CN 975) and no MMA. No MMA odor or other appreciable odor was detected. AC-15C exhibited better light curing sensitivity than Extoral, with twice the double-bond conversion rate. AC-15 was curable scratch-free and mar free after 20 seconds exposure to 500 mW/cm$^2$ light source using VIP, or 40 seconds at 200 mW/cm$^2$ using the same curing light source. Addition of 10% methyl blue colorant in ethanol did not adversely affect the curing. The conversion rate of AC-15C in air and in a nitrogen environment was the same, indicating that it lacked an OIL layer. The Barcol hardness of AC-15C was 77 after curing 40 seconds at 200 mW/cm$^2$ exposure using the Cure-Lite Plus light box system.

Example 11

Preparation of Non-volatile, NOIL Composition AC-35

A composition containing 3.22 g CN975, 1.38 g CN383, 0.4 g TPO, and 2.5 mg MEHQ was prepared. AC-35 formed a scratch-free to human fingernail and tack-free surface to touch after 10 seconds cured at 300 mW/cm$^2$ on Pyramid shade 3.5 composite using the VIP system. AC-36, prepared containing the same amounts of TPO and MEHQ but 2.76 g CN 975 and 1.84 g CN 383, was curable scratch-free to fingernail scratching and tack-free to touch using the same composite base and light cure system after 20 seconds exposure at 300 mW/cm$^2$.

Example 12

Preparation of Non-volatile NOIL Compositions AC-40 and AC-40A

A composition containing 8.9 g CN975, 10.3 g SR349, 7.8 g SR610, 0.9 g CD9052, 2.1 g TPO, and 15 mg MEHQ was prepared. The composition cured into a scratch-free surface after 20 seconds exposure on Pyramid shade 3.5 composite using the VIP curing system set at 500 mW/cm 2. The AC-40 composition also exhibited good stability after storage under water at 60° C., curing in 20 seconds at 300 mW/cm$^2$ on Pyramid composite shade 3.5 after 30 days and 47 days, the latter being comparable to storage for 472 days at 20° C. Addition of 5% CN 383 to the composition (AC-40A) caused a scratch-free surface to form after curing at 300 mW/cm$^2$ for 15–20 seconds, or 10 seconds at 500 mW/cm$^2$ exposure on Pyramid composite using the VIP curing light system. In addition to sealing applications, this composition may also be attractive as a deep cavity filler due to its relatively high viscosity (around 1200 cps at 22° C.).

AC-40 also exhibits good compressive strength of about 282 MPa+/−27 MPa. Compressive strength is determined by preparing a sample in a 6 mm high by 4 mm diameter stainless steel split mold. The sample is cured at 500±50 mW/cm for 60 seconds per side. The disc is heated at 37° C. for 15 minutes. The disc is placed in a 30 ml Nalgene bottle filled with deionized water, and heated for 23 hours at 37° C. The disc is removed, blotted dry, and cooled to room temperature for one hour. An Instron Universal Testing Instrument (model 4465) is used to determine the load reading (kg) at which the sample breaks. The compressive strength is calculated as (load reading (kg)×0.0624)/sample diameter (cm).

AC-40 passed a cytotoxicity assay performed with mouse fibroblast cells on a solid agarose surface. Toxicity, or the lack thereof, was determined by measuring the zone of lysis (if any) around the test sample after incubation at 37° C. in 5% carbon dioxide for 24 hours.

Example 13

Preparation of a Non-volatile NOIL Composition DP20-5

A composition containing 5.2 g DP20, 1.5 g CN383, 2.1 g SR610, 0.5 g CD9052, 0.7 g TPO, and 4.4 mg MEHQ was prepared. The composition cured very rapidly, forming a scratch-free surface after 3–6 seconds at 500 mW/cm 2, 5–10 seconds at 300 mW/cm$^2$, and 60 seconds at 50–100 mW/cm on white paper using the VIP curing light system The DP-20-5 compound also had good compressive strength (51+/−9 MPa as determined using the Instron test system described in the previous Example). It also exhibits a relatively lower viscosity (410 cps at 22° C.) than AC-40. This composition is attractive for use as a protective coating under and around orthodontic application on enamel, or as a margin sealant where rapid curing and flowablity are important considerations Example 14

Preparation of Non-volatile, NOIL Composition Filled DP20-5

Compositions of 10% filler, 20% filler, 30% filler, and 40% filler, and 90%, 80%, 70% and 60% DP-20-5 were made by mixing the appropriate weight amount of filler with the DP20-5 composition described in Example 13 above. The filler used was OX-50 or silanated OX-50. The sample containing 20% OX-50 filled DP20-5 was scratch free after irradiation for 5 seconds at 300 mW/cm$^2$ or for 2 seconds at 500 mW/cm$^2$. The pencil hardness was >5H. These results are similar to those obtained with the neat resin lacking filler. The filler had no noticeable effect on the curability of the resin.

Example 15

Preparation of Non-volatile, NOIL Composition DP60-5

A composition containing 15 g DP60, 4.5 g SR349, 4.5 g SR459, 3 g CN383, 0.9 g CD9052, 2.1 g TPO, and 15 mg MEHQ was prepared. The composition cured to a scratch-free surface in 15 seconds at 500 mW/cm$^2$ and 20 seconds at 300 mW/cm$^2$ exposure using the VIP light gun and after coating the composition on Pyramid shade 3.5 composite. This composition can be used as a flexible coating on dental prosthetic devices, or on dentures. The composition can also be used as a narrow gap filler, where flexibility is desirable.

Example 16

Preparation of Non-volatile NOIL Compositions AC-25 Containing Pentaacrylate and AC-26

A pentaacrylate and two diacrylate composition containing 3 g SR 399, 3 g SR349, 3 g SR610, 0.3 g CD9052, 0.7 g TPO, and 5 mg MEHQ was prepared (AC-25). A similar composition containing a hexaacrylate and two diacrylates was prepared by combining 3 g CN975, 3 g SR349, 3 g SR610, 0.3 g CD9052, 0.7 g TPO, and 5 mg MEHQ (AC-26). Both compositions AC-25 and AC-26 were scratch free after irradiation at 300 mW/cm$^2$ for 20 seconds, or 500 mW/cm$^2$ for 10 seconds. The pencil hardness of both materials was 1H.

Example 17

Evaluation of di-, tri-, and tetra-acrylates in Preparation of NOIL Surfaces

Five resins were selected to compare the ability of diacrylates, triacrylates, and tetraacrylates to prepare NOIL surfaces. Monomer resins were solubilized in acetone at a 1:1 ratio by weight. TPO initiator was added, and the acetone was allowed to evaporate in air for about 60 seconds or more. After 20 seconds evaporation, the acetone was not detectable in terms of weight loss. The compositions were irradiated using either a blue light at 500 mW/cm$^2$ or a bright white light at 200 mW/cm$^2$. The produced surfaces were evaluated as described in the following Table.

| Monomer (# acrylates/ molecule) | TPO weight % | Irradiation time and intensity | Coating surface |
|---|---|---|---|
| SR-355 (4) | 5.6 | 120 seconds, 500 mW/cm$^2$ | Marrable |
|  |  | 120 seconds, 200 mW/cm$^2$ | Almost scratch free |
| SR-355 (4) | 7 | 120 seconds, 500 mW/cm$^2$ | Scratchable |
|  |  | 60 seconds, 200 mW/cm$^2$ | Scratch free |
| SR-351 (3) | 6 | 100 seconds, 500 mW/cm$^2$ | Scratch free |
|  |  | 40 seconds, 200 mW/cm$^2$ | Scratch free |
| SR-502 (3) | 6 | 120 seconds, 500 mW/cm$^2$ | Scratch free |
|  |  | 60 seconds, 200 mW/cm$^2$ | Scratch free |
| SR-350 (3) | 8 | 120 seconds, 500 mW/cm$^2$ | Thick OIL |
|  |  | 120 seconds, 200 mW/cm$^2$ | Thick OIL |
| SR-259 (2) | 10 | 120 seconds, 500 mW/cm$^2$ | Slightly tacky, thin OIL |

As used in this table, "Scratch free" also indicates that the surface was mar free and tack free; "Mar free" also indicates that the surface was tack free but was scratchable. The actual concentration of the TPO is double that shown in the table due to the evaporation of the acetone solvent. Resins made from tri-acrylates or tetra-acrylates could be polymerized to prepare a surface lacking an oxygen inhibition layer. The triacrylate and diacrylate tested under these conditions were not able to produce an acceptable surface.

Example 18

Scratch Resistance Assay of Non-volatile NOIL Sealants

The suitability of NOIL sealants as orthodontic sealants was evaluated using a scratch resistance assay. A surface is rubbed using pencils containing graphite of different hardnesses in an attempt to scratch the surface. The surface is evaluated by what hardness of graphite is required to create a detectable scratch.

This assay is based on ASTM D 3383-00. The sealant was brushed onto a composite disc, and was cured. The pencils were obtained from a Kimberly Graphite Drawing Kit, and had hardnesses according to the following table.

| Softest | | | | | | | | | | | | | | Hardest |
|---|---|---|---|---|---|---|---|---|---|---|---|---|---|---|
| 8B | 7B | 6B | 5B | 4B | 3B | 2B | B | HB | F | H | 2H | 3H | 4H | 5H |

The assay further distinguishes between gouges and scratches. Scratching refers to the hardness needed to indent the surface. Gouging refers to the hardness required to scrape the adhesive from the surface. Oxygen inhibition layers often are easier to scratch than the rest of the cured adhesive, so the scratch/gouge assay is useful to detect the presence of an air inhibition layer on a surface.

The following adhesive compositions were evaluated: (DP20-5, DP-20-5 with a fluorescing agent (DP-20-5F), DP-20-5 with a fluorescing agent and 20% glass ionomer (DP-20-5-FG), Bisco One Step Adhesive System, Filled L/C Sealant, and L/C Sealant. The adhesive compositions were brushed on composite disks made from Bisco Renew Shade A2 Translucent and cured for 2, 5, 10, 20, 30, and 40 seconds using the VIP curing light system before evaluating. The first value in the table is for gouging, the second value is for scratching.

| Product | 2 sec | 5 sec | 10 sec | 20 sec | 30 sec | 40 sec |
|---|---|---|---|---|---|---|
| DP-20-5 | >5H/>5H | >5H/>5H | >5H/>5H | >5H/>5H | >5H/>5H | >5H/>5H |
| DP-20-5F | >5H/>5H | >5H/>5H | >5H/>5H | >5H/>5H | >5H/>5H | >5H/>5H |
| DP-20-5FG | >5H/>5H | >5H/>5H | >5H/>5H | >5H/>5H | >5H/>5H | >5H/>5H |
| One Step | <8B/<8B | >5H/<8B | >5H/<8B | >5H/<8B | >5H/<8B | >5H/<8B |
| Filled L/C Sealant | <8B/<8B | <8B/<8B | >5H/<8B | >5H/<8B | >5H/<8B | >5H/<8B |
| L/C Sealant | <8B/<8B | HB/<8B | 5H/<8B | >5H/<8B | >5H/<8B | >5H/<8B |

Conventional adhesives had significant oxygen inhibition at the surface since the softest pencil used (8B) was able to scratch it. The NOIL DP-20-5 compositions did not have oxygen inhibition layers since even the hardest pencil used (5H) had difficulty scratching the surface. The addition of a fluorescing agent and glass ionomer filler did not detrimentally affect the hardness of the DP-20-5 compositions. These NOIL compositions light cured very quickly, as evidenced by their consistent assay results across the range of time periods tested.

Example 19

Evaluation of Photoinitiators for the Preparation of a NOIL Surface

Six photoinitiators were individually added to a common resin containing 50 g CN-795 (hexafunctional acrylate), 50 g acetone (volatile solvent), 0.1 g Flourad FC-431 (surfactant for leveling), and 0.02 g MEHQ (inhibitor for storage). The following Table lists the initiators.

| Initiator | Chemical name | Absorbance × $10^{-3}$ |
|---|---|---|
| Lucirin TPO (TPO) | 2,4,6-trimethylbenzoyl-diphenylphosphinate | 6 |
| Lucirin TPO-L (TPOL) | ethyl-2,4,6-trimethylbenzoyl-phenylphosphinate | 4 |
| Irgacure 819 (819) | bis(2,4,6-trimethylbenzoyl)-phenylphosphineoxide | 23 |
| Camphorquinone (CQ) | camphorquinone | 11 |
| H-Nu 470 (HNu) | 5,7-diiodo-3-butoxy-6-fluorone | 2960 |
| PAQ | phenanthrenequinone | 466 |

The absorptivity is the absorbance in the range of 400–500 nm in acetonitrile normalized by mass. The higher the value, the higher the absorption in the visible light range. The first three initiators undergo unimolecular bond cleavage upon irradiation. The last three initiators require a co-initiator, such as an amine, to undergo a bimolecular reaction. The initiators (and EDMAB amine if required) were added to the resin. Samples were coated on a white mixing pad, evaporated for greater than 60 seconds, and irradiated at 500 mW/cm$^2$ using a Bisco VIP light curing system. Samples were irradiated for 5 seconds, 10 seconds, 30 seconds, and 10 seconds in the absence of air. The "no air" cure was performed between two Mylar slips, each 0.25 mm thick. The actual concentration of initiator in the resin was double that shown in the table due to the evaporation of the acetone. The surface was evaluated for percent degree of conversion as indicated in the following table.

| | | | DC, % | | | |
|---|---|---|---|---|---|---|
| Initiator | Initiator, % | EDMAB % | 5 sec | 10 sec | 30 sec | 10 sec (no air) |
| CQ | 1 | 1 | 24 | 27 | 30 | 47 |
| CQ | 3 | 3 | 43 | 50 | 58 | 65 |
| TPO | 2 | 0 | 30 | 39 | 39 | 64 |
| TPO | 3 | 0 | 29 | 52 | 52 | 53 |
| 819 | 1.5 | 0 | 44 | 47 | 47 | 57 |
| 819 | 3 | 0 | 49 | 55 | 58 | 65 |
| TPOL | 3 | 0 | 29 | 38 | 57 | 56 |
| HNu | 0.2 | 1 | 0 | 0 | 0 | 23 |
| PAQ | 0.2 | 1 | 0 | 0 | 0 | 33 |

To confirm the observation that the presence of air leads to lower DC values, triplicate samples of resin containing TPO at 3% were irradiated in the presence and absence of air. Average DC values, and the standard deviation were determined as shown in the following Table.

| Irradiation time | Air | DC (std. dev.) |
| --- | --- | --- |
| 10 seconds | Present | 46.9% (3.0%) |
| 30 seconds | Present | 51.6% (4.3%) |
| 10 seconds | Absent | 57.4% (1.3%) |

Resins were prepared and coated on composite disks. After evaporation of the acetone for greater than 60 seconds, the coatings were irradiated for 30 seconds at 300 mW/cm$^2$ bright light. The pencil hardness was measured, as shown in the following Table. All surfaces were found to be tack and fingernail scratch free.

| Initiator | Initiator, % | EDMAB % | Pencil hardness |
| --- | --- | --- | --- |
| CQ | 1 | 1 | 1H |
| CQ | 3 | 3 | >5H |
| TPO | 2 | 0 | 4H |
| TPO | 3 | 0 | 5H |
| 819 | 1.5 | 0 | 4H |
| 819 | 3 | 0 | >5H |
| TPOL | 3 | 0 | 4H |

These results show that initiators other than phosphine oxide, such as camphorquinone, can be used to successfully prepare a NOIL surface.

Example 20

Ortho Shear Bond Strength Assay

DP-20-5 NOIL compositions and L/C Bonding resins were evaluated for their shear strength. NOIL DP20-5 was prepared with and without 0.75 Lumilux Blue (a fluorescent additive) and 20% glass lonomer (X1B44RWG). Bond strength was compared against unfilled and filled L/C Bonding resins.

Human tooth enamel was etched with 37% phosphoric acid semi-gel for 15 seconds. The etchant was washed away with a jet of water, and dried thoroughly with a stream of air. One coat of the aforementioned compositions was applied as a sealant over the etched area by brushing onto the etched enamel surface, and was light cured for 10 seconds at 500 mW/cm$^2$ intensity using the Bisco VIP curing light system. An orthodontic bracket was bonded to the sealed area using bracket adhesive (Lightbond or Phase II) and cured. Bonded samples were placed in a 37° C. deionized water bath for two hours before testing. The shear test results are shown in the following table.

Bond strengths of the tested samples were fairly similar. These results indicate that unfilled and filled NOIL compositions display shear bond strength values suitable for use in orthodontic applications.

Example 21

Fluoride Release Assay

The fluoride release properties of NOIL compositions were compared against L/C sealants. The NOIL sample was DP20-5 containing 20% glass ionomer for fluoride release and 0.75% Lumilux blue for phosphorescence.

Shade disks of DP-20-5 and LC Sealant were prepared as follows. A round stainless steel mold held between polyethylene sheets and glass slabs were used to prepare discs of a fixed size. The discs were cured using two light guns set at 500±50 mW/cm$^2$. A single light gun was positioned over the center of the disc, and irradiated the disc for 20 seconds. Next, the two light guns were positioned at opposing ends of the circle (across the diameter), and irradiated the disc for 10 seconds. The two light guns were moved around the circle to irradiate the disc for a total of four times of 10 seconds (position of the two light guns around the circular discs: 0 and 180 degrees, then 90 and 270 degrees, then 135 and 315 degrees, and finally 45 and 225 degrees), in addition to the 20 second irradiation in the center). The top glass plate was removed, and the curing process repeated. The specimen was heated at 37±3° C. for 15±1 minutes. A diamond burr was used to drill a hole near the edge of the disks. The disk was sonicated in acetone to remove any air inhibited layer that may be present. The diameter and height of the disk was measured with a caliper, and the mass of the disk was determined using an analytical balance. A wire was threaded through the hole and twisted/turned such that the disk can be propped upright within a vial. An aqueous solution of sodium chloride (0.2M, 10 ml) was added to each vial, the vials were capped, and placed at 37° C. for 1 hour. Fluoride release was determined using a fluoride sensitive electrode immersed in a 50/50 TISAB/sample mixture. Three tests of each sample were performed. The results are shown in the following table.

| Sample | Fluoride release (μg/cm$^2$) |
| --- | --- |
| L/C Sealant test #1 | 0.178 |
| L/C Sealant test #2 | 0.172 |
| L/C Sealant test #3 | 0.153 |
| DP-20-5test #1 | 0.286 |
| DP-20-5test #2 | 0.262 |
| DP-20-5test #3 | 0.280 |

These results show that the NOIL sealants such as DP-20-5 with fluoride glass can release significantly more fluoride than the conventional L/C sealant. NOIL sealants can therefore be used in applications where fluoride release is desirable or required.

| Bracket adhesive | L/C Sealant | Filled L/C Sealant | Unfilled DP-20-5 | Filled DP-20-5 with Flourescer |
| --- | --- | --- | --- | --- |
| Lightbond | 22.85 ± 2.0 MPa | 23.04 ± 6.4 MPa | 23.08 ± 1.7 MPa | 20.96 ± 1.3 MPa |
| Phase II | 23.23 ± 5.7 MPa | 25.02 ± 5.9 MPa | 20.27 ± 2.8 MPa | 21.12 ± 1.8 MPa |

Example 22

Use of NOIL as a Top Surface Over a Composite

A composite can be placed appropriately in a dental restoration procedure according to the manufacturer's instructions. The final layer of composite is placed and adapted to the cavosurface margin, shaped, and contoured to the desired final form. A thin coating of a NOIL composition such as AC-40 or DP-20-5 is gently applied using a soft brush over the surface of the composite and the surrounding enamel. The NOIL-coated surface is then light cured using an appropriate light source and time of irradiation (e.g. visible blue light from a VIP light gun at 600 mW/sec$^2$ for 20–40 seconds or less). The produced surface will have a smooth, glossy surface. Further, such surface can be obtained without the need for shaping the composite with burs or abrasives as required in conventional composite applications, thereby avoiding potential damage to surrounding tooth tissue structure while also further minimizing patient time in the treatment room.

Example 23

Use of NOIL Over a Low Viscosity Composite

A low viscosity or flowable composite can be placed appropriately in a dental restoration procedure. The final layer of composite is placed and adapted to the cavosurface margin, shaped, and contoured to the desired final form. The composite is light cured for a short period of time such as 5 seconds to eliminate flow of the composite material. A thin coating of NOIL (such as DP-20-5) is gently applied using a soft brush over the surface of the composite and the surrounding enamel. The surface is then light cured using an appropriate light source and time of irradiation (e.g. visible blue light at 600 mW/sec$^2$). The produced surface will have a smooth, glossy surface.

Example 24

Use of NOIL as a Root Surface Coating

A root surface requiring desensitization can be isolated, and scrubbed with a pumice and cavity cleanser slurry using a cotton pellet, foam pellet, or microbrush. The root surface can additionally be etched with phosphoric acid for 15 seconds if desired. A thin coating of NOIL (such as DP-20-5) or a filled sample for non-slumping purposes is gently applied using a soft brush over the root surface. The NOIL surface is thinned with a gentle stream of air, and light cured using an appropriate light source and time of irradiation (e.g. for 10 seconds with visible blue light at 600 mW/sec$^2$ using the VIP curing light system)

Example 25

Use of NOIL on Dental Appliances

Shear bond strength (SBS) of NOIL formulas AC-40 and DP20-5 were tested and compared to that of Fortify Plus. The following substrates were tested: enamel, dentin, composite, uncured composite, Rex III, porcelain, amalgam, acrylic, and Itself. The following techniques were used.

Enamel—Enamel was pumiced, rinsed and dried. Enamel was etched with 37% phosphoric acid semi-gel for 15 seconds before rinsing and drying. One coat of Fortify Plus, AC-40 or DP20-5 was applied and light cured for 20 seconds, 20 seconds and 5 seconds respectively at 500 mW/cm$^2$. Post was bonded and sheared after being stored in 37° C. water for two hours.

Dentin—Dentin was polished on moistened 600 grit sanding paper for 30 seconds, rinsed and dried. Dentin was etched for 15 seconds using 32% phosphoric acid semi-gel. Dentin was rinsed and kept moist. 5–7 coats of All Bond 2 Primer A&B mixture were applied to moist dentin. Primed surface was lightly air-dried. One coat of Fortify Plus, AC-40 or DP20-5 was applied and light cured for 20 seconds at 500 mW/cm$^2$. Post was bonded and sheared after being stored in 37° C. water for two hours.

Amalgam and RexIII—Amalgam and Rex III were polished on moistened 600 grit sanding paper for 30 seconds, rinsed and dried. Surface was microetched using the Accuprep to achieve a uniform surface. One coat of Fortify Plus, AC-40 or DP20-5 was applied and light cured for 20 seconds, 20 seconds and 5 seconds respectively at 500 mW/cm$^2$. Post was bonded and sheared after being stored in 37° C. water for two hours.

Composite and Acrylic—Composite and acrylic were polished on moistened 600 grit sanding paper for 30 seconds, rinsed and dried. Surface was microetched using the Accuprep to achieve a uniform surface. Surface was etched with 32% phosphoric acid semi-gel for 15 seconds before rinsing and drying. One coat of Fortify Plus, AC-40 or DP20-5 was applied and light cured for 20 s, 20 s and 5 s respectively at 500 mW/cm$^2$. Post was bonded and sheared after being stored in 37° C. water for two hours.

Porcelain—Porcelain was polished on moistened 600 grit sanding paper for 30 seconds, rinsed and dried. The surface was microetched using the Accuprep to achieve a uniform surface. The surface was etched with 4% hydrofluoric acid semi gel for 4 minutes, rinsed and dried. Generous amounts of porcelain primer was applied to the surface and allowed to air-dry. One coat of Fortify Plus, AC-40 or DP20-5 was applied and light cured for 20 seconds, 20 seconds and 5 seconds respectively at 500 mW/cm$^2$. Post was bonded and sheared after being stored in 37° C. water for two hours.

Uncured composite—A preparation was done in acrylic using a high speed handpiece and burr. The preparation was etched with Accuprep and 32% phosphoric acid semi-gel. Etched surface was treated with One Step according to manufacturers instructions. Renew A2 Translucent was filled into the preparation. One coat of Fortify Plus, AC-40 or DP20-5 was applied and light cured for 40s at 500 mW/cm$^2$. Post was bonded and sheared after being stored in 37° C. water for two hours.

Itself—Substrates of cured Fortify Plus, AC-40 and DP20-5 were set into acrylic. Composite and acrylic were polished on moistened 600 grit sanding paper for 30 seconds, rinsed and dried. Surface was microetched using the Accuprep to achieve a uniform surface. Surface was etched with 32% phosphoric acid semi-gel for 15 seconds before rinsing and drying. One coat of Fortify Plus, AC-40 or DP20-5 was applied to their respective substrates and light cured for 20 seconds, 20 seconds and 5 seconds respectively at 500 mW/cm$^2$. Post was bonded and sheared after being stored in 37° C. water for two hours.

The results of the shear bond strength (SBS) assays are shown in the following table, where numerical values are in MPa. A #5 gel cap (bonding area 0.1684 cm$^2$) was used in each of the foregoing tests along with an Instron (Model 4466) shear bond machine set to a crosshead speed of 5 mm/min, and the shear bond strength (SBS) was calculated in MPa by dividing the peak load by bonding area. The mean and standard deviations were calculated for five replications (N=5) for each test.

| Substrate | DP20-5 | AC-40 | Fortify+ |
|---|---|---|---|
| Dentin | 13.81 ± 2.9 | 19.12 ± 2.7 | 14.82 ± 9.5 |
| Enamel | 21.58 ± 4.4 | 25.51 ± 3.3 | 24.25 ± 3.1 |
| Acrylic | 11.81 ± 4.5 | 17.62 ± 2.0 | 12.82 ± 1.8 |
| Rex III | 12.63 ± 1.2 | 17.80 ± 0.1 | 11.41 ± 1.9 |
| Amalgam | 11.84 ± 1.4 | 14.98 ± 2.3 | 11.47 ± 1.9 |
| Itself | 9.21 ± 3.2 | 14.97 ± 3.7 | 18.28 ± 3.3 |
| Composite | 17.37 ± 3.1 | 15.35 ± 7.7 | 16.83 ± 4.7 |
| Porcelain | 17.72 ± 1.7 | 17.58 ± 3.2 | 14.50 ± 1.2 |
| Uncured composite | 16.74 ± 3.1 | 13.69 ± 3.0 | 22.13 ± 7.5 |

In general, DP20-5 and AC-40 performed as well or better than Fortify +, within experimental error.

The location of failure has been of particular interest in comparing the performance of dental products. Sample sets consisted of 5 specimens. Most failures occurred in the substrate (SUB) or at the interface of the substrate and sealant (S/S). There are a few occasions where it appears that there was failure at the sealant layer (SEAL). There is one case in which there appears to be a failure at the sealant and post interface (S/P). These observations are summarized in the following table.

| Substrate | DP20-5 | AC-40 | Fortify+ |
|---|---|---|---|
| Dentin | 1SEAL; 4S/S | 2SUB; 2S/S; 1SEAL | 1SUB; 4S/S |
| Enamel | 1SUB; 4S/S | 2SUB; 3S/S | 3SUB; 2S/S |
| Acrylic | 3S/S; 2SEAL | 4S/S; 1SEAL | 5S/S |
| Rex III | 5S/S | 5S/S | 5S/S |
| Amalgam | 5S/S | 3SUB; 2S/S | 1SUB; 4S/S |
| Itself | 4SUB; 1S/S | 4SUB; 1S/S | 5SUB |
| Composite | 5SUB | 5SUB | 5SUB |
| Porcelain | 5SUB | 5SUB | 5SUB |
| Uncured composite | 5SUB | 3SUB; 1S/S; 1S/P | 5SUB |

Example 26

Use of NOIL in Fingernail or Toenail Repair Applications

DP-20-5 was tested as a fingernail repair composition as follows. A thin layer of DP20-5 was coated on a human fingernail with brushing until a smooth surface was obtained. The composition was exposed to 500 mW/cm$^2$ light intensity using VIP curing light system for about 5 seconds. The composition cured into a smooth shiny surface that was hard to the touch.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention.

What is claimed is:

1. A light curing dental composition comprising a multiacrylate compound and a photo initiator, wherein:
   the multiacrylate compound comprises at least five acrylate functionalities per molecule; and
   the composition does not comprise methyl methacrylate, wherein the composition cures to form a surface lacking an oxygen inhibition layer upon exposure to visible light, and wherein the photo initiator is present at a concentration of at least about 6 weight percent of the composition.

2. The composition of claim 1, wherein the initiator is a phosphine oxide compound.

3. The composition of claim 1, wherein the initiator is 2,4,6-trimethylbenzoyldiphenylphosphine oxide (TPO).

4. The composition of claim 1, wherein the initiator is present at a concentration of at least about 7 weight percent of the composition.

5. The composition of claim 1, wherein the multiacrylate compound comprises five acrylate functionalities per molecule.

6. A light curing dental composition comprising a multiacrylate compound and a photo initiator, wherein:
   the multiacrylate compound comprises at least six acrylate functionalities per molecule; and
   the composition does not comprise methyl methacrylate, wherein the composition cures to form a surface lacking an oxygen inhibition layer upon exposure to visible light.

7. The composition of claim 1, wherein the multiacrylate compound is selected from the group consisting of a hexafunctional aromatic urethane acrylate oligomer, a caprolactone modified dipentaerythritol hexaacrylate, and dipentaerythritol pentaacrylate.

8. The composition of claim 1, wherein the multiacrylate compound is present at a concentration of at least about 20 weight percent of the composition.

9. The composition of claim 1, wherein the multiacrylate compound is present at a concentration of at least about 30 weight percent of the composition.

10. The composition of claim 1, further comprising a co-monomer.

11. The composition of claim 10, wherein the co-monomer is selected from the group consisting of a monoacrylate compound, a diacrylate compound, a triacrylate compound, and a tetraacrylate compound.

12. A light curing dental composition comprising a multiacrylate compound and a photo initiator, wherein:
   the multiacrylate compound comprises at least five acrylate functionalities per molecule;
   a co-monomer selected from the group consisting of caprolactone acrylate, tripropylene glycol diacrylate, ethoxylated bisphenol A diacrylate, and polyethylene glycol diacrylate, trimethylolpropane triacrylate, and ditrimethylolpropane tetraacrylate; and
   the composition does not comprise methyl methacrylate, wherein the composition cures to form a surface lacking an oxygen inhibition layer upon exposure to visible light.

13. The composition of claim 1, further comprising a filler.

14. The composition of claim 1, further comprising a nanofiller.

15. The composition of claim 1, further comprising glass particles.

16. The composition of claim 1, further comprising an acrylated amine compound.

17. The composition of claim 1, further comprising a diluent.

18. The composition of claim 17, wherein the diluent is acetone, ethanol, water, a mixture of acetone and water, a mixture of ethanol and water, a mixture of ethanol and acetone, or a mixture of ethanol, water, and acetone.

19. A light curing dental composition comprising a multiacrylate compound and a photo initiator, wherein:
the multiacrylate compound comprises at least five acrylate functionalities per molecule and is selected from the group consisting of a hexafunctional aromatic urethane acrylate oligomer, a caprolactone modified dipentaerythritol hexaacrylate, and dipentaerythritol pentaacrylate; and
the composition does not comprise methyl methacrylate,
wherein the composition cures to form a surface lacking an oxygen inhibition layer upon exposure to visible light, and
wherein the multiacrylate compound is the hexafunctional aromatic urethane acrylate oligomer.

20. A light curing dental composition comprising a multiacrylate compound and a photo initiator, wherein:
the multiacrylate compound comprises at least five acrylate functionalities per molecule;
a co-monomer selected from the group consisting of a monoacrylate compound, a diacrylate compound, a triacrylate compound, and a tetraacrylate compound; and
the composition does not comprise methyl methacrylate,
wherein the composition cures to form a surface lacking an oxygen inhibition layer upon exposure to visible light; and
wherein the multiacrylate compound is a hexafunctional aromatic urethane acrylate oligomer, and the co-monomer is the di-acrylate compound.

21. The composition of claim 20, wherein the di-acrylate is ethoxylated bisphenol A diacrylate.

22. The composition of claim 21, further comprising polyethylene glycol (600) diacrylate.

* * * * *